US008313759B2

(12) United States Patent
Schwarz

(10) Patent No.: US 8,313,759 B2
(45) Date of Patent: Nov. 20, 2012

(54) IMPLANTABLE OR INSERTABLE MEDICAL DEVICES CONTAINING MISCIBLE POLYMER BLENDS FOR CONTROLLED DELIVERY OF A THERAPEUTIC AGENT

(75) Inventor: Marlene C. Schwarz, Auburndale, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2152 days.

(21) Appl. No.: 10/382,552

(22) Filed: Mar. 6, 2003

(65) Prior Publication Data

US 2004/0175406 A1    Sep. 9, 2004

(51) Int. Cl.
*A61F 13/00* (2006.01)
*A01N 61/00* (2006.01)

(52) U.S. Cl. ............................................. 424/422; 514/1

(58) Field of Classification Search ........................ None
See application file for complete search history.

(56) References Cited

U.S. PATENT DOCUMENTS

| | | | | |
|---|---|---|---|---|
| 4,847,324 A * | 7/1989 | Creasy | ............................. | 525/57 |
| 4,946,899 A | 8/1990 | Kennedy et al. | ............... | 525/244 |
| 5,258,020 A | 11/1993 | Froix | ................................ | 623/1 |
| 5,304,121 A | 4/1994 | Sahatjian | ......................... | 604/53 |
| 5,616,608 A | 4/1997 | Kinsella et al. | ................ | 514/449 |
| 5,716,981 A | 2/1998 | Hunter et al. | .................. | 514/449 |
| 5,733,925 A | 3/1998 | Kunz et al. | ..................... | 514/449 |
| 5,741,331 A | 4/1998 | Pinchuk | ........................... | 623/11 |
| 5,837,008 A * | 11/1998 | Berg et al. | ....................... | 128/898 |
| 5,856,367 A | 1/1999 | Barrows et al. | .................. | 521/64 |
| 5,879,697 A | 3/1999 | Ding et al. | ..................... | 424/422 |
| 5,954,706 A | 9/1999 | Sahatjian | ....................... | 604/509 |
| 6,099,562 A | 8/2000 | Ding et al. | ..................... | 623/1.46 |
| 6,110,483 A * | 8/2000 | Whitbourne et al. | ......... | 424/423 |
| 6,280,411 B1 | 8/2001 | Lennox | .................... | 604/103.05 |
| 6,306,419 B1 * | 10/2001 | Vachon et al. | ................. | 424/422 |
| 6,335,029 B1 | 1/2002 | Kamath et al. | ................ | 424/423 |
| 6,443,980 B1 * | 9/2002 | Wang et al. | .................... | 623/1.11 |
| 6,997,885 B2 * | 2/2006 | Lubock et al. | ................. | 600/567 |
| 7,175,873 B1 * | 2/2007 | Roorda et al. | ................ | 427/2.14 |
| 7,396,539 B1 * | 7/2008 | Hossainy et al. | ............. | 424/423 |
| 2002/0032477 A1* | 3/2002 | Helmus et al. | .................. | 623/1.2 |
| 2002/0045706 A1 | 4/2002 | Houston et al. | ................ | 525/100 |
| 2002/0107330 A1* | 8/2002 | Pinchuk et al. | ................. | 525/242 |
| 2003/0104030 A1* | 6/2003 | Igaki et al. | ..................... | 424/426 |
| 2004/0033251 A1* | 2/2004 | Sparer et al. | ................... | 424/425 |
| 2004/0047911 A1* | 3/2004 | Lyu et al. | ....................... | 424/487 |

FOREIGN PATENT DOCUMENTS

| | | | |
|---|---|---|---|
| WO | WO 98/56312 | | 12/1998 |
| WO | 9908729 A1 | | 2/1999 |
| WO | WO 00/21584 | | 4/2000 |
| WO | WO 00/32255 | | 6/2000 |
| WO | WO 03/011250 A1 | | 2/2003 |
| WO | WO 2004/000381 A1 | | 12/2003 |

OTHER PUBLICATIONS

Schantz, Steffan, Structure and Mobility in Poly(ethylene oxide)/Poly(methylmethacrylate) Blends Investigated by 13C solid-state NMR, Macromolecules, 1997, 30, 1419-1425.*
Domb, Abraham J., Degradable Polymer BLends. I. Screening of Miscible Polymers, Journal of Polymer Science: Part A: Polymer Chemistry, vol. 31, 1973-1981 (1993).*
PSLC, Poly(vinylidene fluoride), pp. 1-3, date available Aug. 19, 2002.*
Pimbert, Sylvie, Polymer 43 (2002) 3295-3302.*
Bar, Frits, et al., J Biomed Mater Res, 52, 193-198, 2000.*
Dong, Limin, et al., Macromolecules, 27, 5912-5918, 1994.*
Hans Adam Schneider, "Conformational Entropy Contributions to the Glass Temperature of Blends of Miscible Polymers," *Journal of Research of the National Institute of Standards and Technology*, vol. 102, No. 2, Mar.-Apr. 1997, pp. 229-248.
Miscible Polymer Blends. http://www.psrc.usm.edu/macrog/blen.htm.
Immiscible Polymer Blends. http://www.psrc.usm.edu/macrog/iblend.htm.
L.H. Sperling, *Polymeric Multicomponent Materials: An Introduction* (New York: John Wiley & Sons), pp. 284-285.
*Diblock and Triblock Copolymers*, pp. 141-151.
James F. Beecher et al., "Morphology and Mechanical Behavior of Block Polymers," J. Polymer Sci, Part C, No. 26 (1969), pp. 117-134.
Richard J. Spontak et al., "Phase Behavior of Ordered Diblock Copolymer Blends: Effect of Compositional Heterogeneity," *Macromolecules*, 1996, vol. 29, pp. 4494-4507.
Kohtaro Kimishima et al., "Control of Self-Assembled Structures in Binary Mixtures of A-B Diblock Copolymer and A-C Diblock Copolymer by Changing the Interaction between B and C Block Chains," *Macromolecules*, 1999, vol. 32, pp. 2585-2596.
Hong G. Jeon et al., "Microphase and Macrophase Transitions in Binary Blends of Diblock Copolymers," *Macromolecules*, 1999, vol. 32, pp. 1803-1808.

* cited by examiner

*Primary Examiner* — Brian-Yong S Kwon
*Assistant Examiner* — Lyndsey Beckhardt
(74) *Attorney, Agent, or Firm* — Mayer & Williams PC; David B. Bonham; Keum J. Park

(57) ABSTRACT

A therapeutic-agent release region is described, which comprises: (i) a first phase comprising a plurality of miscible polymers that are miscible with one another and (ii) a second phase comprising an additional polymer, which can be immiscible with any or all of the plurality of miscible polymers or a blend of the miscible polymers. Also described is a therapeutic-agent-releasing medical device, which comprises: (a) an implantable or insertable medical device substrate; (b) the above release region, disposed over at least a portion of the implantable or insertable medical device substrate, and (c) a therapeutic agent. The release region regulates the rate of release of the therapeutic agent from the medical device upon implantation or insertion of the device into a patient. Also described are methods for making an implantable or insertable medical device, for administering a therapeutic agent to a patient, and for modulating the release rate of a therapeutic agent.

21 Claims, No Drawings

IMPLANTABLE OR INSERTABLE MEDICAL DEVICES CONTAINING MISCIBLE POLYMER BLENDS FOR CONTROLLED DELIVERY OF A THERAPEUTIC AGENT

FIELD OF THE INVENTION

The present invention relates to implantable or insertable medical devices in which miscible polymer blends are used to control delivery of one or more therapeutic agents.

BACKGROUND OF THE INVENTION

Numerous medical devices have been developed for the delivery of therapeutic agents to the body.

In accordance with some delivery strategies, a therapeutic agent is provided (a) within a polymeric carrier layer and/or (b) beneath a polymeric barrier layer that is associated with an implantable or insertable medical device. Once the medical device is placed at the desired location within a patient, the therapeutic agent is released from the medical device at a rate that is dependent upon the nature of the polymeric carrier and/or barrier layer.

The desired release profile for the therapeutic agent is dependent upon the particular treatment at hand, including the specific condition being treated, the specific therapeutic agent selected, the specific site of administration, and so forth. As a result, there is a continuing need for polymeric regions, including polymeric barrier layers and carrier layers, which are able to provide a range of therapeutic agent release rates.

SUMMARY OF THE INVENTION

According to a first aspect of the present invention, a therapeutic-agent-releasing medical device is provided, which comprises: (a) an implantable or insertable medical device substrate; (b) a release region disposed over at least a portion of the implantable or insertable medical device substrate; and (c) a therapeutic agent. The release region regulates the rate of release of the therapeutic agent from the medical device upon implantation or insertion of the device into a patient and comprises (i) a first phase comprising a plurality of miscible polymers, the plurality of miscible polymers being miscible with one another and (ii) a second phase comprising an additional polymer.

The miscible polymers can be, for example, homopolymers, copolymers, or both homopolymers and copolymers. In many embodiments, a pair of miscible polymers is used in the release region. Examples of miscible polymer pairs include: (a) poly(vinyl butyral)/poly(vinyl pyrrolidone); (b) poly(2,6-dimethyl-1,4-phenylene oxide)/polystyrene; (c) tetramethyl bisphenol A polycarbonate/polystyrene; (d) poly(ethylene oxide)/poly(methyl methacrylate); (e) poly(vinylidene fluoride)/poly(methyl methacrylate); (f) polystyrene/poly(vinylmethyl ether); (g) poly(methyl methacrylate)/poly(styrene-co-acrylonitrile); (h) poly(vinyl chloride)/poly(ethylene-co-vinyl acetate); and (i) poly(styrene-co-maleic anhydride)/poly(styrene-co-acrylonitrile).

The additional polymer can also be, for example, a homopolymer or a copolymer. For example, the additional polymer can be a copolymer comprising (i) one or more polyolefin polymer chains and (ii) one or more vinyl aromatic polymer chains.

In some embodiments, the release region is a carrier layer that comprises the therapeutic agent(s). In other embodiments, the release region is a barrier layer disposed over a therapeutic-agent-containing region that comprises the therapeutic agent.

Medical devices include catheters, guide wires, balloons, filters, stents, stent grafts, vascular grafts, vascular patches, shunts, and intraluminal paving systems. The medical device can be adapted, for example, for implantation or insertion into the coronary vasculature, peripheral vascular system, esophagus, trachea, colon, biliary tract, urinary tract, prostate or brain.

Beneficial therapeutic agents for the practice of the present invention include anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

According to another aspect of the present invention, a method of making therapeutic-agent-releasing medical devices like those described above is provided. The method comprises: (a) providing a solution comprising: (i) a solvent, (ii) the plurality of miscible polymers and (iii) the additional polymer; (b) applying the solution to a surface of the implantable or insertable medical device substrate; and (c) removing the solvents from the solution to form the release region. Solvent spraying is one beneficial technique for applying the above solution.

In some embodiments (for example, where a carrier layer is formed), the solution further comprises the therapeutic agent. In other embodiments (for example, where a barrier layer is formed), the solution is applied over a therapeutic-agent-containing region.

According to another aspect of the present invention, a method of administering a therapeutic agent to a patient is provided. The method comprises (a) providing a therapeutic-agent-releasing medical device like that described above and (b) implanting or inserting the therapeutic-agent-releasing medical device of into the patient. In certain embodiments, the medical device is inserted into the vasculature, where the therapeutic agent is released in the treatment of restenosis.

According to yet another aspect of the present invention, a method of modulating the release rate of a therapeutic agent is provided. The method comprises (a) providing a release region like that above over a substrate; and (b) modulating the rate of release of the therapeutic agent by varying the weight fraction of at least one of the miscible or additional polymers, relative to the total weight of the release region. In certain embodiments, the weight fractions corresponding to the miscible polymers are varied, while the weight fraction corresponding to the immiscible polymer is held constant. In certain other embodiments, the weight fraction corresponding to the immiscible polymer is varied relative to the total weight of the release region, along with the weight fraction corresponding to one or more of the miscible polymers.

One advantage of the present invention is that implantable or insertable medical devices can be provided, which are able to provide therapeutic agent release over a variety of time frames.

Another advantage of the present invention is that effective strategies can be provided for modulating, or "tuning," the release profile of a therapeutic agent.

These and other embodiments and advantages of the present invention will become immediately apparent to those of ordinary skill in the art upon review of the Detailed Description and claims to follow.

DETAILED DESCRIPTION OF THE INVENTION

The present invention relates to implantable or insertable medical devices that provide for the release of one or more therapeutic agents, to methods for making such devices, and to methods for modulating the rate at which therapeutic agent is released from such devices.

According to one aspect of the present invention, a therapeutic-agent release region is provided, which comprises: (i) a first phase comprising a plurality of miscible polymers, which are miscible with one another and (ii) a second phase comprising an additional polymer, also referred to herein as an immiscible polymer, which can be immiscible with any or all of the plurality of miscible polymers or a blend of the miscible polymers.

The release region can be provided in a number of configurations. For example, the release region can constitute the entirety of the medical device, or it can constitute only a portion of the medical device, for example, one or more medical device layers (e.g., one or more coating layers), one or more medical device components or portions thereof, and so forth.

By "release region" is meant a region that regulates the rate of release of a therapeutic agent. Release regions are typically either carrier regions or barrier regions. A "carrier region" is a region which contains at least one therapeutic agent and from which the therapeutic agent is released. A "barrier region" is a region that is disposed between a source of therapeutic agent and a site of intended release, which controls the rate at which the therapeutic agent is released.

For instance, in some embodiments of the present invention, an outer carrier layer is disposed over at least a portion of an implantable or insertable medical device substrate. Upon implantation or insertion of the resulting device, the therapeutic agent is released from the carrier layer in a controlled fashion. In other embodiments, a therapeutic-agent-containing layer and a barrier layer are provided over at least a portion of an implantable or insertable medical device substrate. Because the barrier layer is disposed over the therapeutic-agent-containing layer, the barrier layer acts to control release of the therapeutic agent from the medical device upon implantation or insertion of the same.

As noted above, the release region comprises: (i) a first phase comprising a plurality of miscible polymers, which are miscible with one another and (ii) a second phase comprising an additional polymer, also referred to herein as an immiscible polymer, which is can be immiscible with any or all of the plurality of miscible polymers or a blend of the miscible polymers.

One way of determining whether two or more polymers are miscible or immiscible is to observe glass transition temperature. Glass transition temperature can be measured by any of a number of techniques, such as differential scanning calorimetry, or dynamic mechanical analysis. For example, where two homopolymers, polymer A and polymer B, are miscible with one another, a blend of these polymers will exhibit a single phase and a single glass transition temperature, which is generally located somewhere between the glass transition temperature of polymer A and that of polymer B, dependent upon the relative weight fractions of polymer A and polymer B within the blend. In contrast, where polymer A and polymer B are immiscible with one another, a blend of these polymers will exhibit two glass transition temperatures, one corresponding to a polymer A rich phase and one corresponding to a polymer B rich phase. Of course, this technique requires that the glass transition temperatures of polymer A and polymer B be sufficiently well separated from one another. In the event that they are not, microscopic analysis of the phases, using for example, optical microscopy, electron microscopy (e.g. TEM), or atomic force microscopy may be used to observe phase separation.

The polymers need not be miscible over all possible composition ranges for use in connection with the present invention. For example, a blend of polymer A and polymer B may be immiscible over a range of 20% polymer A to 80% polymer A, while being miscible over the remaining ranges (i.e., less than 20% polymer A and more than 80% polymer A).

The miscible polymers will typically occupy a first phase within the release region, while the immiscible polymer will occupy a distinct second phase. These phases are typically observable using microscopy techniques such as those discussed above.

A morphological progression like the following is sometimes observed for two-phase polymeric systems: (a) when the volume of the first phase is small relative to that of the second phase, the first phase forms small spherical domains within the second phase; (b) as the volume of the first phase is increased relative to that of the second phase, the sizes of the first phase spherical domains grow, in due course becoming cylindrical in shape; (c) a further increase in the volume of the first phase relative to that of the second phase sometimes results in the formation of a lamellar structure; (d) as the volume of the first phase continues to increase relative to that of the second phase, cylindrical domains of the second phase are formed within the first phase, eventually becoming (e) spherical domains of the second phase within the first phase. Of course, the above examples are merely illustrative and other domain morphologies are possible.

The miscible and immiscible polymers for use in connection with the present invention can be selected from a wide variety of polymers, which may be, for example, homopolymers or copolymers (e.g., random, alternating or block copolymers). Polymer configurations include, cyclic, linear and branched configurations. Branched configurations include star-shaped configurations (e.g., configurations in which three or more chains emanate from a single branch point), comb configurations (e.g., graft copolymers having a main chain and a plurality of branching side chains) and dendritic configurations (including arborescent or hyperbranched copolymers).

Specific examples of polymers include the following: polycarboxylic acid polymers and copolymers including polyacrylic acids; acetal polymers and copolymers; acrylate and methacrylate polymers and copolymers; cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-butadiene copolymers, acrylonitrile-styrene copolymers, acrylonitrile-butadiene-styrene copolymers, styrenebutadiene-styrene copolymers and styrene-isobutylene-styrene copolymers, polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-l-ene and polyisobutylene), poly-4-methyl-pen-l-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; urethane polymers and copolymers; p-xylylene polymers and copolymers; polyiminocarbonates; copoly(ether-esters) such as polyethylene oxidepolylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid.

Some specific examples of miscible polymer pairs include the following:

(a) poly(vinyl butyral)/poly(vinyl pyrrolidone) (PVB/PVP);

(b) poly(2,6-dimethyl-1,4-phenylene oxide)/polystyrene (PPO/PS)

(c) tetramethyl bisphenol A polycarbonate/polystyrene (PC/PS);

(d) poly(ethylene oxide)/poly(methyl methacrylate) (PEO/PMMA);

(e) poly(vinylidene fluoride)/poly(methyl methacrylate) (PVF/PMMA);

(f) polystyrene/poly(vinylmethyl ether) (PS/PVME);

(g) poly(methyl methacrylate)/poly(styrene-co-acrylonitrile) (PMMA/SAN);

(h) poly(vinyl chloride)/poly(ethylene-co-vinyl acetate) (PVC/EVAc); and (i) poly(styrene-co-maleic anhydride)/poly(styrene-co-acrylonitrile) (SMA/SAN).

Some specific examples of immiscible polymers for use in the present invention (with immiscibility obviously being dependent on the miscible polymers that are selected) include copolymers comprising at least two polymer chains A and B. The A polymer chains are preferably soft elastomeric components which are based upon one or more polyolefins or another polymer with a glass transition temperature at or below room temperature, such as polymer chains of ethylene, propylene, butylene, isobutylene, and/or polybutadiene, silicone polymer chains, an alkyl acrylate polymer chains, and so forth. The B polymer chains are preferably hard thermoplastic chains with glass transition temperatures significantly higher than the elastomeric A block that, when combined with the soft A chains, are capable of, inter alia, altering or adjusting the hardness of the resulting copolymer to achieve a desired combination of qualities. Preferred B polymer chains are polymers of vinyl aromatics, such as chains made from monomers of styrene

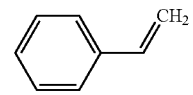

and/or styrene derivatives (e.g., α-methylstyrene, ring-alkylated styrenes or ring-halogenated styrenes or other substituted styrenes where one or more substituents are present on the aromatic ring), collectively referred to herein as "styrenic blocks" or "styrenic chains". Examples include diblock copolymers, triblock copolymers (e.g., where a central A block is capped on either end by B blocks), star copolymers (e.g., where a central A block is capped by B blocks) and other branched block copolymers, for example, dendritic block copolymers (e.g., where a central branched A block is capped by B blocks) or graft copolymers (e.g., where a number of B blocks originate from an A block main chain).

In some particular embodiments of the present invention the immiscible polymer is selected from (a) polystyrene-polyisobutylene-polystyrene triblock copolymers, which, along with other polymers appropriate for the practice of the present invention, are described, for example, in U.S. Pat. No. 5,741,331, U.S. Pat. No. 4,946,899 and U.S. Pat. Appln. No. 20020107330, each of which is hereby incorporated by reference in its entirety; and (b) a copolymer containing one or more blocks of polystyrene and one or more random polymer blocks of ethylene and butylene, for example, a polystyrene-polyethylene/butylene-polystyrene (SEBS) block copolymer, available as Kraton™ G series polymers available from Kraton Polymers. A further immiscible polymer for use in the present invention is an n-butyl methacrylate (BMA) polymer available from Aldrich Chemical.

According to another aspect of the invention, a method is provided for modulating the release rate of a therapeutic agent from a release region like those described above.

For example, the release rate can be modulated by varying the weight fraction of at least one of the miscible or immiscible polymers, relative to the total weight of the release region. In some embodiments, for instance, the weight fractions of the miscible polymers are varied, while the weight fraction of the immiscible polymer is held constant. For example, a release region containing 25 wt % miscible polymer A, 25 wt % miscible polymer B, and 50 wt % immiscible polymer C can be modified to contain 35 wt % miscible polymer A, 15 wt % miscible polymer B, and 50 wt % immiscible polymer C. Without wishing to be bound by theory, it is believed that the release of the therapeutic agent from the medical device will depend upon the diffusion rate of the therapeutic agent through the release region. Continuing with the example where two miscible polymers A and B form a single polymer phase within the release region, the range of diffusion rates should lie between the diffusion rates that are observed were the single polymer phase is formed solely from polymer A or is formed solely from polymer B. As a consequence, various drug release rates are observed by using different blend ratios of miscible polymers A and B.

Other possibilities clearly exist. For example, in some embodiments, the collective weight fraction corresponding to the miscible polymers and the collective weight fraction corresponding to the immiscible polymer(s) are varied. For example, a release region containing 25 wt % miscible polymer A, 25 wt % miscible polymer B, and 50 wt % immiscible polymer C can be modified to contain 35 wt % miscible polymer A, 35 wt % miscible polymer B, and 30 wt/o immiscible polymer C. Many other possibilities clearly exist.

The release rate can also be modulated by varying the type and/or molecular weight of the miscible and immiscible polymers used within the release region. Moreover, the release region thickness can be varied to modulate the release of therapeutic agent. In addition, multiple release regions can be employed to achieve this end. Furthermore, where a carrier region is employed, a therapeutic-agent concentration gradient can be established within the carrier region to modulate release of therapeutic agent.

The release characteristics that are ultimately of interest are the release characteristics within the subject, for example, within a mammalian subject. However, it is well known in the art to test the release characteristics within an experimental system that gives a good indication of the actual release characteristics within the subject. For example, aqueous buffer systems are commonly used for testing release of therapeutic agents from vascular devices.

Preferred implantable or insertable medical devices for use in connection with the release regions of the present invention include catheters (for example, renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including GDC—Guglilmi detachable coils—and metal coils), vascular grafts, myocardial plugs, patches, pacemakers and pacemaker leads, heart valves, biopsy devices, or any coated substrate (which can comprise, for example, glass, metal, polymer, ceramic and combinations thereof) that is implanted or inserted into the body, either for procedural use or as an implant, and from which therapeutic agent is released.

The medical devices contemplated for use in connection with the present invention include drug delivery medical devices that are used for either systemic treatment or for the localized treatment of any mammalian tissue or organ. Non-limiting examples are tumors; organs including but not limited to the heart, coronary and peripheral vascular system (referred to overall as "the vasculature"), lungs, trachea, esophagus, brain, liver, kidney, bladder, urethra and ureters, eye, intestines, stomach, pancreas, ovary, and prostate; skeletal muscle; smooth muscle; breast; cartilage; and bone.

One particularly preferred medical device for use in connection with the present invention is a vascular stent, which delivers therapeutic agent into the vasculature, for example, in the treatment of restenosis. As used herein, "treatment" refers to the prevention of a disease or condition, the reduction or elimination of symptoms associated with a disease or condition, or the substantial or complete elimination a disease or condition. Preferred subjects are mammalian subjects and more preferably human subjects.

A wide range of therapeutic agent loadings can be used in connection with the medical devices of the present invention, with the amount of loading being readily determined by those of ordinary skill in the art and ultimately depending, for example, upon the condition to be treated, the nature of the therapeutic agent itself, the means by which the therapeutic agent is administered to the intended subject, and so forth.

"Therapeutic agents," "pharmaceutically active agents," "pharmaceutically active materials," "drugs" and other related terms may be used interchangeably herein and include genetic therapeutic agents, non-genetic therapeutic agents and cells. Therapeutic agents may be used singly or in combination.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; and (o) agents that interfere with endogenous vasoactive mechanisms.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include (a) plasmids, (b) viral vectors such as adenovirus, adenoassociated virus and lentivirus, and (c) non-viral vectors such as lipids, liposomes and cationic lipids.

Cells for use in connection with the present invention include cells of human origin (autologous or allogeneic), including stem cells, or from an animal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including $\alpha$-antagonists such as prazosin and bunazosine, $\beta$-antagonists such as propranolol and $\alpha/\beta$-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and $\beta$-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-$\alpha$ pathway agents such as polyanionic agents (heparin, fucoidin), decorin, and TGF-$\beta$ antibodies, EGF pathway agents such as EGF antibodies, receptor antagonists and chimeric fusion proteins, TNF-$\alpha$ pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincrisfine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

Numerous techniques are available for forming the release regions of the present invention. For example, where the selected combination of polymers has thermoplastic characteristics, a variety of standard thermoplastic processing techniques can be used to form the release region, including compression molding, injection molding, blow molding, spinning, vacuum forming and calendaring, as well as extrusion into sheets, fibers, rods, tubes and other cross-sectional profiles of various lengths. As a specific example, a release region coating can be co-extruded along with an underlying medical device or portion thereof. If the therapeutic agent is stable at processing temperatures, then it can be combined with the combination of polymers, for example, by extrusion, prior to thermoplastic processing, producing a therapeutic agent containing release region.

Release regions can also be formed using solvent-based techniques, in which the above-described miscible and immiscible polymers are dissolved or dispersed in a solvent system prior to region formation.

Where solvent-based techniques are used, the solvent system that is selected will contain one or more solvent species. The solvent system preferably is a good solvent for the polymers and, where included, for the therapeutic agent as well. The particular solvent species that make up the solvent system may also be selected based on other characteristics including drying rate and surface tension.

Preferred solvent-based techniques include, but are not limited to, solvent casting techniques, spin coating techniques, web coating techniques, solvent spraying techniques, dipping techniques, techniques involving coating via mechanical suspension, including air suspension, ink jet techniques, electrostatic techniques, and combinations of these processes.

Typically, a solution containing solvent and polymers (and, in some cases, a therapeutic agent) is applied to a medical device substrate to form a release region (for example, a carrier layer or a barrier layer). The medical device substrate typically corresponds to all or a portion of an implantable or insertable medical device, to which the release region is applied.

Where appropriate, techniques such as those listed above can be repeated or combined to build up a release region to a desired thickness. The thickness of the release region can be varied in other ways as well. For example, in one preferred process, solvent spraying, coating thickness can be increased by modification of coating process parameters, including increasing spray flow rate, slowing the movement between the substrate to be coated and the spray nozzle, providing repeated passes and so forth.

In the case where, for example, a carrier layer is established, a therapeutic agent can be included in the above-described polymer solution if desired, and hence co-established with the carrier layer. Alternatively, the therapeutic agent can be dissolved or dispersed within a solvent, and the resulting solution contacted with a previously formed polymeric layer (which contains the miscible and immiscible polymers), for example, using one or more of the application techniques described above (e.g., dipping, spraying, etc.).

In the case where, for example, a barrier layer is established, the release region is formed over a therapeutic-agent-containing region. In some embodiments, the underlying therapeutic-agent-containing region can comprise one or more polymers, which can be selected, for example, from the polymers listed above. As such, the therapeutic-agent-containing region can be established using solvent-based techniques such as those discussed above. In other embodiments, the therapeutic-agent-containing region beneath the barrier layer is established without an associated polymer. For example, the therapeutic agent can simply be dissolved or dispersed in a liquid, and the resulting solution/dispersion contacted with a substrate, for instance, using one or more of the above-described application techniques (e.g., dipping, spraying, etc.).

Where the release region is formed using a solvent-based technique, it is preferably dried after application to remove the solvents. The release region typically further conforms to any underlying surface during the drying process.

Although various embodiments are specifically described herein, it will be appreciated that modifications and variations of the present invention are covered by the above teachings and are within the purview of the appended claims without departing from the spirit and intended scope of the invention.

The invention claimed is:

1. A therapeutic-agent-releasing medical device comprising:
   (a) an implantable or insertable medical device substrate;
   (b) a therapeutic agent; and
   (c) a release region in the form of a layer disposed over at least a portion of the implantable or insertable medical device substrate, said release region comprising (i) a first phase comprising a pair of miscible polymers that form a single polymer phase within the release region, said pair of miscible polymers being miscible with one another and selected from homopolymers, alternating copolymers, random copolymers and combinations thereof, and (ii) a second phase comprising an additional polymer which is not a block copolymer; wherein said first and second phases are in the same layer, wherein the volume of the first phase is less than the volume of the second phase, wherein said release region is a two-phase polymeric system, wherein the first phase forms cylindrical domains within the second phase or wherein the first and second domains form a lamellar structure, wherein said release region regulates the rate of release of said therapeutic agent from the medical device upon implantation or insertion of the device into a patient, and wherein said pair of miscible polymers is a pair of miscible polymers selected from the following: (a) poly(styrene-co-maleic anhydride)/poly(styrene-co-acrylonitrile), (b) poly(2,6-dimethyl-1,4-phenylene oxide)/polystyrene, (c) tetramethyl bisphenol A polycarbonate/polystyrene, (d) poly(ethylene oxide)/poly(methyl methacrylate), (e) polystyrene/poly(vinylmethyl ether), (f) poly(methyl methacrylate)/poly(styrene-co-acrylonitrile), and (g) poly(vinyl chloride)/poly(ethylene-co-vinyl acetate).

2. The therapeutic-agent-releasing medical device of claim 1, wherein at least one of said miscible polymers is a homopolymer.

3. The therapeutic-agent-releasing medical device of claim 1, wherein at least one of said miscible polymers is a copolymer.

4. The therapeutic-agent-releasing medical device of claim 1, wherein said additional polymer is a homopolymer.

5. The therapeutic-agent-releasing medical device of claim 1, wherein said additional polymer is a copolymer.

6. The therapeutic-agent-releasing medical device of claim 1, wherein said release region is a barrier layer disposed over a region that comprises said therapeutic agent.

7. The therapeutic-agent-releasing medical device of claim 1, wherein said release region is a carrier layer comprising said therapeutic agent.

8. The therapeutic-agent-releasing medical device of claim 1, wherein said implantable or insertable medical device is selected from a catheter, a guide wire, a balloon, a filter, a stent graft, a vascular graft, a vascular patch, a shunt, and an intraluminal paving system.

9. The therapeutic-agent-releasing medical device of claim 1, wherein said implantable or insertable medical device is a stent.

10. The therapeutic-agent-releasing medical device of claim 1, wherein said implantable or insertable medical device is adapted for implantation or insertion into the coronary vasculature, peripheral vascular system, esophagus, trachea, colon, biliary tract, urinary tract, prostate or brain.

11. The therapeutic-agent-releasing medical device of claim 1, wherein said therapeutic agent is selected from the group consisting of an anti-thrombotic agent, an anti-proliferative agent, an anti-inflammatory agent, an anti-migratory agent, an agent affecting extracellular matrix production and organization, an antineoplastic agent, an anti-mitotic agent, an anesthetic agent, an anti-coagulant, a vascular cell growth promoter, a vascular cell growth inhibitor, a cholesterol-lowering agent, a vasodilating agent, and an agent that interferes with endogenous vasoactive mechanisms.

12. A method of forming the therapeutic-agent-releasing medical device of claim 1, comprising: (a) providing a solution comprising: (i) one or more solvent species, (ii) said miscible polymers and (iii) said additional polymer; (b) applying said solution to a surface of said implantable or insertable medical device substrate; and (c) removing said solvents from said solution to form said release region.

13. The method of claim 12, wherein said solution further comprises said therapeutic agent.

14. The method of claim 12, wherein said solution is applied over a region that comprises said therapeutic agent.

15. The method of claim 12, wherein said solution is applied by a solvent spraying technique.

16. A method of administering a therapeutic agent to a patient comprising (a) providing the therapeutic-agent-releasing medical device of claim 1 and (b) implanting or inserting the therapeutic-agent-releasing medical device of into said patient.

17. The method of claim 16, wherein said medical device is selected from a catheter, a guide wire, a balloon, a filter, a stent, a stent graft, a vascular graft, a vascular patch, a shunt, and an intraluminal paving system.

18. The method of claim 17, wherein said medical device is inserted into the vasculature.

19. The method of claim 18, wherein said therapeutic agent is released in the treatment of restenosis.

20. The therapeutic-agent-releasing medical device of claim 1, wherein said additional polymer is immiscible with all of said pair of miscible polymers.

21. The therapeutic-agent-releasing medical device of claim 1, wherein said additional polymer comprises polyisobutylene.

\* \* \* \* \*

UNITED STATES PATENT AND TRADEMARK OFFICE
CERTIFICATE OF CORRECTION

| | | |
|---|---|---|
| PATENT NO. | : 8,313,759 B2 | |
| APPLICATION NO. | : 10/382552 | |
| DATED | : November 20, 2012 | |
| INVENTOR(S) | : Marlene C. Schwarz | |

It is certified that error appears in the above-identified patent and that said Letters Patent is hereby corrected as shown below:

Specification, col. 10, line 3, after "ocreotide," change "TGF-αpathway", to --TGF-β pathway--.

Signed and Sealed this
Twelfth Day of February, 2013

Teresa Stanek Rea
*Acting Director of the United States Patent and Trademark Office*